United States Patent [19]
Resnick

[11] Patent Number: 5,807,724
[45] Date of Patent: Sep. 15, 1998

[54] DEGRADATION OF PETROLEUM HYDROCARBONS WITH ORGANISMS ENCAPSULATED IN WAX

[76] Inventor: Joseph A. Resnick, R.D. 1, Box 415A, Natrona Heights, Pa. 15065

[21] Appl. No.: 487,589

[22] Filed: Jun. 7, 1995

Related U.S. Application Data

[63] Continuation of Ser. No. 201,059, Feb. 24, 1994, abandoned, which is a continuation of Ser. No. 888,515, May 26, 1992, abandoned, which is a continuation of Ser. No. 390,363, Aug. 7, 1989, abandoned.

[51] Int. Cl.⁶ .............................. C12N 11/02; C12N 1/26; C12N 11/04; C12S 1/00
[52] U.S. Cl. .................... 435/177; 435/182; 435/248; 435/249; 435/255.4; 435/262.5; 435/281; 210/601
[58] Field of Search ..................................... 435/177, 182, 435/248, 249, 250, 251, 262.5, 281, 288, 255.4; 210/601

[56] References Cited

U.S. PATENT DOCUMENTS

| | | | |
|---|---|---|---|
| 3,860,490 | 1/1975 | Guttag | 435/182 X |
| 3,870,599 | 3/1975 | Azarowicz | 435/281 |
| 4,415,661 | 11/1983 | Thirumalachar et al. | 435/281 X |
| 4,521,515 | 6/1985 | Hata | 435/281 X |
| 4,681,851 | 7/1987 | Baumgarten et al. | 435/182 X |
| 4,734,439 | 3/1988 | Reischl | 435/41 X |
| 5,298,264 | 3/1994 | Edens et al. | 435/182 X |

OTHER PUBLICATIONS

Hamley, G.G., The Condensed Chemical Dictionary, 8th edition, VNR, New York, 1971, p. 936.

*Primary Examiner*—David M. Naff
*Attorney, Agent, or Firm*—Bartony Hare & Edson

[57] ABSTRACT

Organisms that degrade hydrocarbon-based substances are encapsulated in wax to form organism-containing wax microshells that are used for removing oil-based substances such as oil spills on land and water. The organism is preferably of the genus Candida that produce lipase. The microshell may contain nutrients that sustain the organism. The wax is paraffin wax or beeswax, and the microshell may be coated with talc or carbon powder to provide insulation and to prevent one microshell from sticking to another. When used for remediating an oil spill on water, the microshells are preferably contained in a buoyant container that acts as a flotation device. The flotation device may contain flotation means such as gas-filled microballoons that facilitate flotation.

13 Claims, 6 Drawing Sheets

DEGRADATION OF PETROLEUM HYDROCARBONS WITH ORGANISMS ENCAPSULATED IN WAX

This application is a continuation of application Ser. No. 08/201,059, filed Feb. 24, 1994, now abandoned, which is a continuation of application Ser. No. 08/888,515, filed May 26, 1992, now abandoned, which is a continuation of application Ser. No. 08/390,363, filed Aug. 7, 1989, now abandoned.

TECHNICAL FIELD

The invention relates to the subject of remediation of chemical and petrochemical spills on land, in standing or moving water, e.g., oceans, lakes, rivers, etc., though use of microencapsulated species of microbes e.g., those representative of the genus *Candida lipolytica; C. guilliermondii;* and *C. yarrowia*.

BACKGROUND

Since the advent of the drilling of the first oil well in Pithole Pa., near Oil City, Pa. in the late 19th Century, man has continued to improve the methods by which greater volumes of crude oil may be extracted from the earth. Such production of crude oil in such remote places as Saudi Arabia, Africa; Egypt; Iran; Venezuela; Australia, etc., require transportation of the crude oil to processing centers located near large metropolitan centers where demand for petrolatum-based products is high. Such transportation may be facilitated through pipelines, supertanker sailing ships, land based tanker trucks, etc.

Throughout the decades many, many accidental oil spills have occurred, resulting in devastation to marine and terrestrial life, and the environment or biosphere (ecosystems) in general. The object of my invention is to provide a method and means whereby such accidental spills may be contained in such a way as to remediate the spill, while simultaneously preventing devastation to the biosphere and specific marine ecosystems. Other aspects of my invention, e.g., use of same in food and chemical production processes are also described.

DISCLOSURE OF INVENTION

The instant invention teaches a method and means for enabling the remediation and removal (neutralization, if you will) of spilled oils or fats (lipids) from land, moving or standing fluids (lakes, oceans, seas, standing aquifers, etc.) slurries, or semi-solid, processed manufactures, or from food substances.

My invention relates to my discovery of a three particular species of the yeasts which possess the capability to produce an enzyme, lipase, which is capable of breaking down hydrocarbon-based substances, e.g., crude oil and other petroleum distillates, either paraffin-based or possessing other peculiar chemical bases. The particular strains I use in reducing my discovery to practice were identified through a Field and Technical Search which was conducted for me, under contract, by the National Aeronautics and Space Administration's IAC, the NASA Industrial Application Center at the University of Pittsburgh, Profile #7209, which is herein incorporated by reference. The particular species I have named above, and their ability to produce lipase (and accomplish hydrocarbon and N-Aldehane degradation in to base components, e.g., H; C; and O) has been well established in the literature.

In my experiments I have found that of the 300+species of Candida, three particular species of the genus *Candida lipolytica*, more specifically, *C. albicans; C. guilliermondii;* and *C. yarrowia*, have performed exceedingly well in degrading sample oils in my laboratory. I selected and specified these particular species for claiming in my discovery, as they possess certain properties with regard to nutrient requirements (some require no nutrient; are aerobic or anerobic), possess the ability to produce lipase across a broad temperature range (>−10 F. to >+68 F.), and are capable of maintaining basal cellular activity in salt or fresh waters. Of course, other species and organisms of and not of the genus C. could and may also be used as a component in the bioremediation device, instant, and in that regard the examples cited above should be interpreted as being illustrative, rather than limiting.

The species cited above may be used i.e., encapsulated in their freeze-dried or reconstituted forms in the treatment and remediation of oil spills on land and in water. Common brewers yeast, in the freeze dried state, will also perform to degrade hydrocarbons.

A second, more important aspect of my discovery is the ability to place living organisms 2 in a protective "shell" 1, as it were, thereby allowing the shell containing the organism to be placed in standing or moving aquifers where oil spills 3 have occurred. Such placement enables the organism to gain proximity to the oil (containing hydrocarbons) where it may produce lipase and digest the hydrocarbons (crude oils) thereby preventing damage to the environment, marine life, and other elements of the ecosystem and biosphere. A third aspect of the invention brought about through such placement in the microcontainer is that the viable cell(s) maintains its integrity by preventing it the organism from osmosing too much water across its cell membrane, preventing the organism's demise (these species lack water intake control mechanisms such that when placed in water the microbe has a propensity to take on so much water that it eventually explodes (and dies).

Placement of the reconstituted organisms 2 in the microshell 1 is accomplished through use of the Kornfeld Rotary Reactor, a device developed by NASA (see NASA Tech Briefs, MFS-28214, entitled Rotary Reactor Makes Large Latex Particles) which is in the public domain, or through utilization of any number of encapsulating devices or processes, e.g., the Vanderhoff Rotary Reactor (also a NASA technology), by microshell manufacturers e.g., KMS Industries of Ann Arbor, Mich., or Micro-Pak, Inc. of N.Y.; Insulated Technologies Corp. of Philadelphia, Pa. or any encapsulation method accomplished by one reasonably skilled in the art of microencapsulation technologies.

An additional feature of the invention is that the device, or components thereof, may be used to prevent the buildup of paraffin wax upon and in the well head and casings of producing oil wells (provided the container, sic., well casing or well head is comprised of materials containing the instant manufacture—which is now made possible); to remove or alter/treat specific confined oils (lipids or fats) or petroleum distillates, in systems such as back-wash processes, oil separation units, food processing systems (for the removal of specific esters, monomers, polymers, co-polymers (cholesterol, for example, excess of which is injurious to human health, could be removed from processed cheeses or other dairy products), production of medical pharmaceuticals, eta., or in any situation where it may be desired to remove oil-based substances from standing or moving fluids; from manufacturing processes, or from processed solids, semi-solids or slurries (yogurt, for example).

Accordingly, the present invention provides encapsulated microbes or cryptobiotic microbes. The microbes possess the ability to produce chemical-degrading enzymes. Preferably, the microbes are capable of producing lipase (a hydrocarbon-degrading enzyme).

Preferably, the microencapsulated organisms are contained in a semipermeable, hydrophobic microsphere to protect the organisms from contact with aqueous fluids. The encapsulating microsphere of the present invention may be fabricated from a paraffin or paraffin-based substance(s). Preferably, the encapsulating microsphere of the present invention may is fabricated of beeswax, natural or synthesized. The microspheres preferably have a diameter between 0.20 and 1000 micrometers;

The microencapsulated organisms of the present invention may be sustained, if necessary, by organic or inorganic nutrients, particularly, fructose, glucose, and/or amulose. The microorganisms may be aerobic or anaerobic.

The present microencapsulated organism also preferably include an insulation coating, e.g., talc or powdered carbon.

Preferably, the encapsulated microbes are contained in a buoyant container to act as a flotation device. Preferably, the container has affixed thereupon fastening means or mechanisms. An example of a suitable fastening means is a Velcro® fastening system. The fastening means may also comprise of a manufactured orifice, slot or receptacle or a curved protrusion. The fastening means enables attachment of two or more similar flotation devices. The present invention thus provides an efficient and convenient delivery system enabling use of a single encapsulated-microbe-containing flotation device or multiple fastened devices.

The flotation device may be, for example, fabricated of plastic compartments. The flotation device may also have flotation means such as multiple layers or groupings of gas-filled microballoons to facilitate flotation. Such microballoons may, for example, be fabricated polyvinylchloride or polybutylcarbonate.

The floatation device may also include means of insulating the organisms from injury arising from environmental elements such as temperature extremes. The present invention may also include a signalling means comprising systems sufficient to inform the user as to the operability of the present invention, as exampled by the teachings of U.S. Pat. No. 4,424,911.

MODES OF CARRYING OUT THE INVENTION

Figure 1:
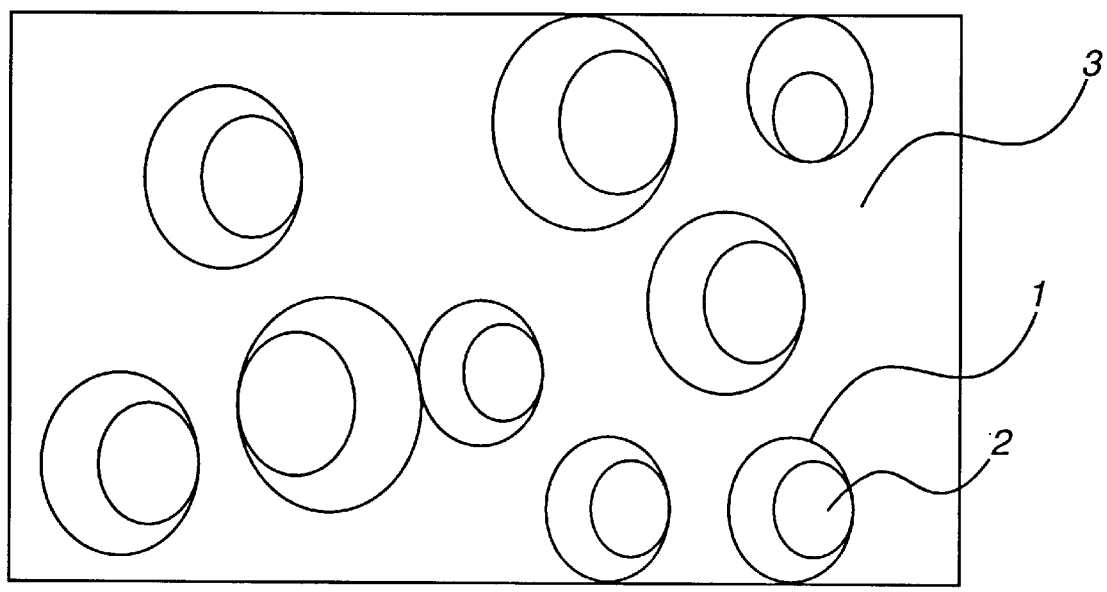
FIG. 1 is a plan view of part of one embodiment of the invention showing the organism 2 being encapsulated in a microshell 1 having an aspect ratio of 0.024 $\mu$m and an outside diameter of 30 $\mu$m (representative). The term "aspect ratio" refers to the ratio of the wall thickness (i.e., outer diameter minus inner diameter) to the inner diameter of the microsphere.

With reference to FIG. 1, an example of the instant manufacture comprises a microscopic-sized container 1, or microballoon, such as may be produced though use of the Kornfeld Rotary Reactor, the Vanderhoff Reactor, or other such scintillating or rotary processes, which range in size from 0.20 $\mu$m to 1000 $\mu$m, comprised of a material, e.g., beeswax which is a hydrophobic, which will permit passage of petroleum substances to gain access to the organism, yet preventing entrance of water to the proximity of the organism.

Figure 1A:
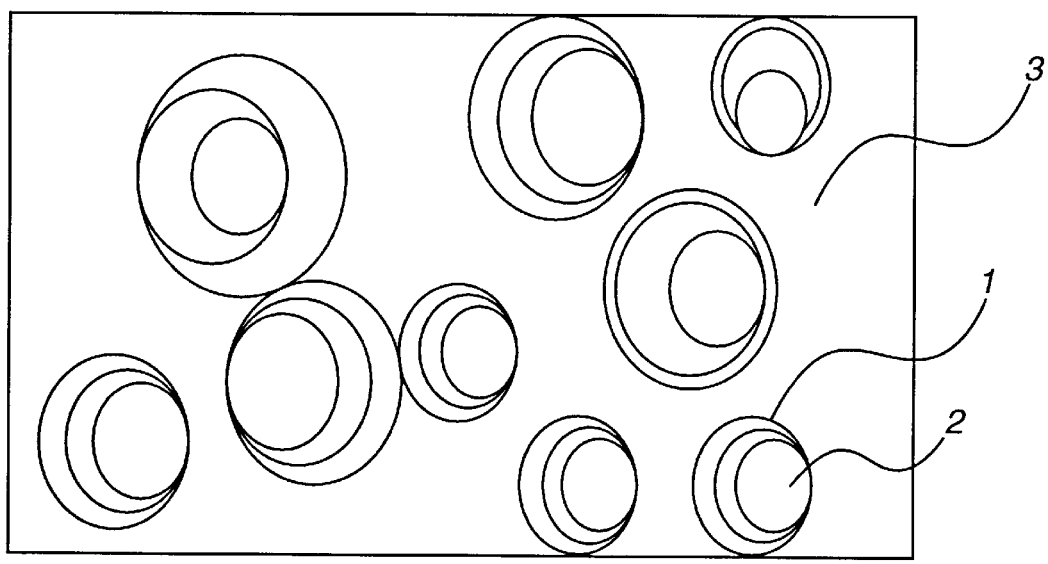
FIG. 1A is an elevational views of the microshell 1 containing the organism 2, the shell 1 being comprised of lipids, paraffin, or any other substance which will protect the organism from contacting the water, yet allowing osmosis of aromatic and non-aromatic hydrocarbons and N-alkanes across and through the microshell, enabling access to the proximity of the organism 2.
Figure 2:
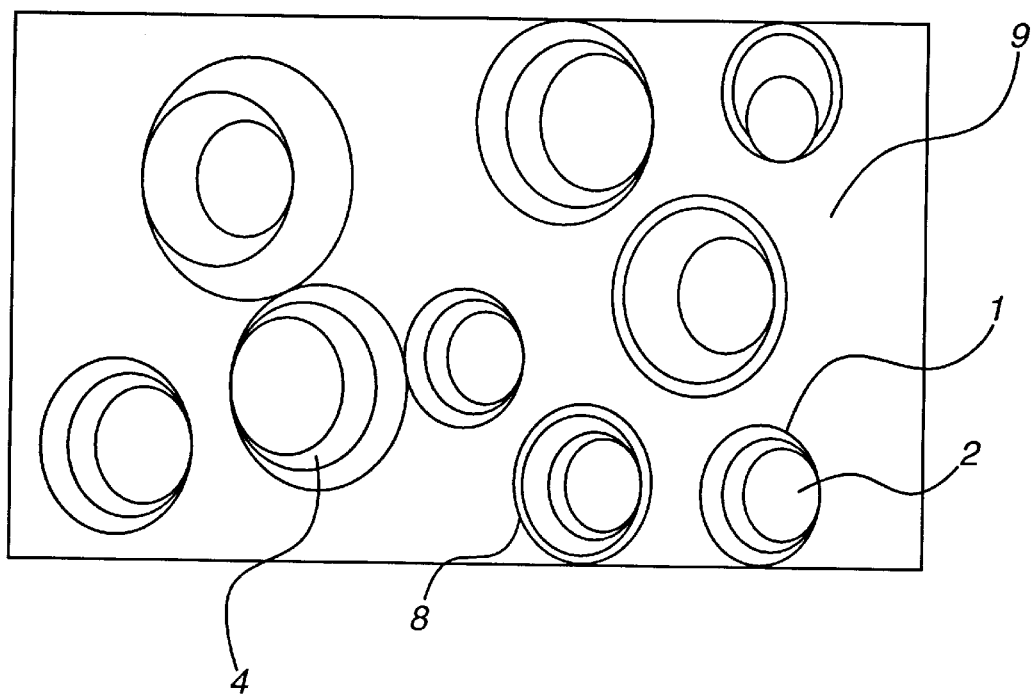
FIG. 2 is a plan view of the organism 2 and the microshell 1 containing a nutrient 4 suspended in a fluid (oil) 9 representative of how the crude oils, or constituent elements contained therein (N-alkanes, aromatic and non-aromatic hydrocarbons) act to move across the semipermeable microsphere and into the proximity of the organism.

With reference to FIG. 1A, an example of the microshell 1 containing the organism 2 is represented. The representative organism, *C. lipolytica*, for example, may be placed within the microballoon, as may certain nutrients 4 required to sustain the organism (oxygen, glucose, etc.), simultaneously with production of the microballoon.

With reference to FIGS. 1 and 1A, the substances, nutrients 4, contained within the microballoon may be ambient air, rarified gasses, nutrient gasses, or chemical nutrients, e.g. fructose or glucose. Further, the shell 1 may be comprised of any substance, being hydrophobic, capable of preventing entrance of undesired fluids from making contact with the organism contained in the microshell, yet which will permit passage of certain substances, e.g., esthers, phenols, glycols, isomers, polymers, monomers, etc. into the proximity of the organism. For example, the shell comprising the instant manufacture is comprised of paraffin based wax. In a future embodiment, beeswax, which possesses certain other desirable molecular properties which paraffin wax does not possess will be used to comprise the shells.

The reason for this is apparent, as the molecular density of beeswax differs from that of paraffin-based wax. For example, it may be more desirable to use a shell made of beeswax for preventing the build-up of paraffin in well heads, or for treating spills in saltwater, as saltwater has a different density than freshwater and it may be desired to treat a spill which has settled to a certain level in salt and fresh waters, where the waters have been joined in a confluence.

For example, in Alaska, runoff water from melting glaciers is deposited into the ocean: At the point of interface of the freshwater with saltwater, a distinctly chemical difference in the waters is obvious (one fluid will "float" on the other—because of the difference in molecular densitites of both fluids). In this example one can see where the ability to control the density of the materials comprising the shell 1 is of significant import. In addition, it is possible to control the aspect ratio of the shell during the manufacturing phase. This is significant in terms of controlling the density of the final product(s) I plan to market. For example, the shell of the instant invention has an aspect ratio of 0.24 $\mu$m, and this feature of the device can be controlled during the manufacture process. It is further possible to control the thickness of the shell itself (some oils, e.g., crude would require the shell to be less dense, than, say phenols or esthers), while simultaneously controlling the overall size of the shell, both I.D. and O.D. Further, during the final phase of the manufacturing process, the device is "coated" with a substance, e.g., talc 8, which aids in cooling the microshell and further prevents one microshell from bonding to another by virtue of proximity. Although I teach the use of talc in the instant embodiment, other powdered substances, e.g., carbon powder, may be better suited than talc for such insulation/protection applications. The ideal coating is easily determined by one of reasonable skill, and it would be obvious for one to use any reliable insulator, which is what the talc 8 becomes when so applied, in reducing the instant manufacture to practice.

Figure 3:
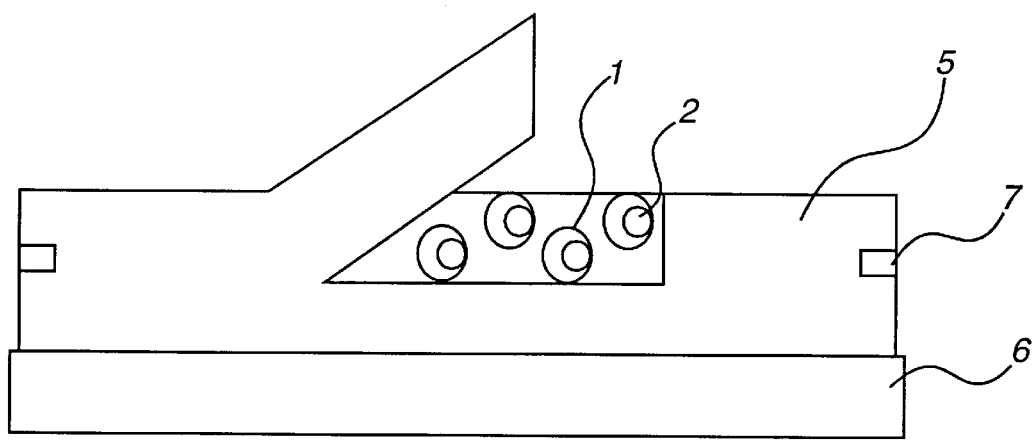
FIG. 3 is a plan view showing the microshell 1 containing the organism 2 being contained in a sack or oblongated container 5 enabling easy placement of the combined devices into the proximity of small oil spills, e.g., those which might occur in foundries or machine shops. The significance of this embodiment is that in view of such placement ease of transportation and mobility is obtained, as is the added feature of reuse (the device is reusable so long as the organism has sufficient nutrient (oil, etc.). A similar object is now marketed under the Trademark of PIG manufactured by New Pig Corporation of Tipton, Pa. The PIG utilizes absorptive mechanisms clay) and certain fibres contained in flexible, oblongated sacks as a means of absorbing oil spills. The PIG performs well on land based oil spills, but not in water where oil has been accidentally spilled. A problem with the PIG is that, although it absorbes the oil, the PIG containing the oil then becomes a "pollutant" and must be dealt with accordingly. The present invention on the other hand, possesses a number of advantages over the present art in that it, i) will operate in both water and on land; ii) is reusable; and iii) is environmentally beneficial in that the microbial action of the present invention reduces the harmful elements of the hydrocarbon-bearing fluids to their base elements, hydrogen, carbon, etc., and returns same to the environment in a neutral, non-polluting state.
Figure 3A:
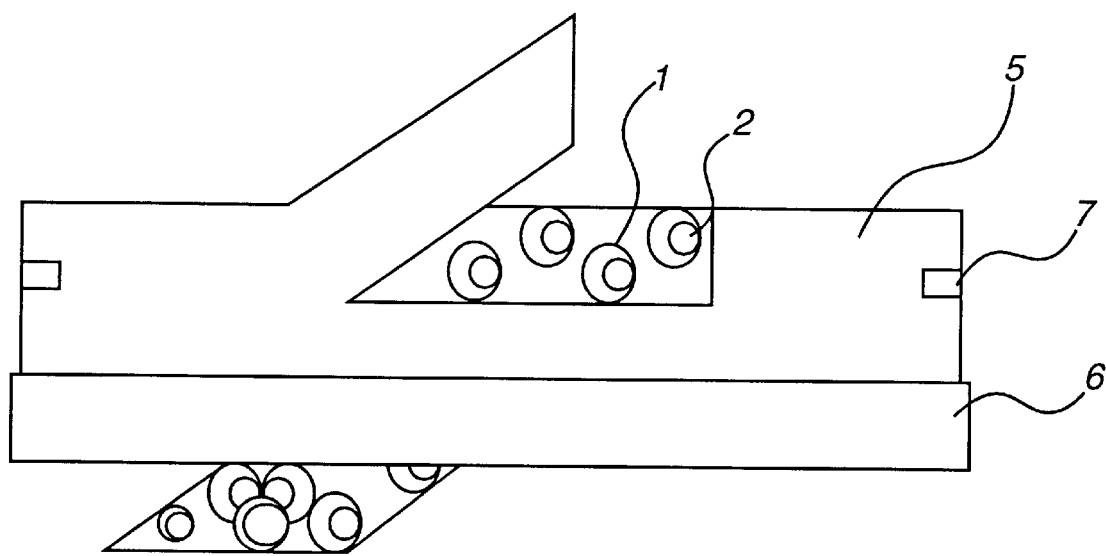
FIG. 3A is an elevational view of FIG. 3 showing the addition of floatation means 6 and locking mechanisms 7.
Figure 4:
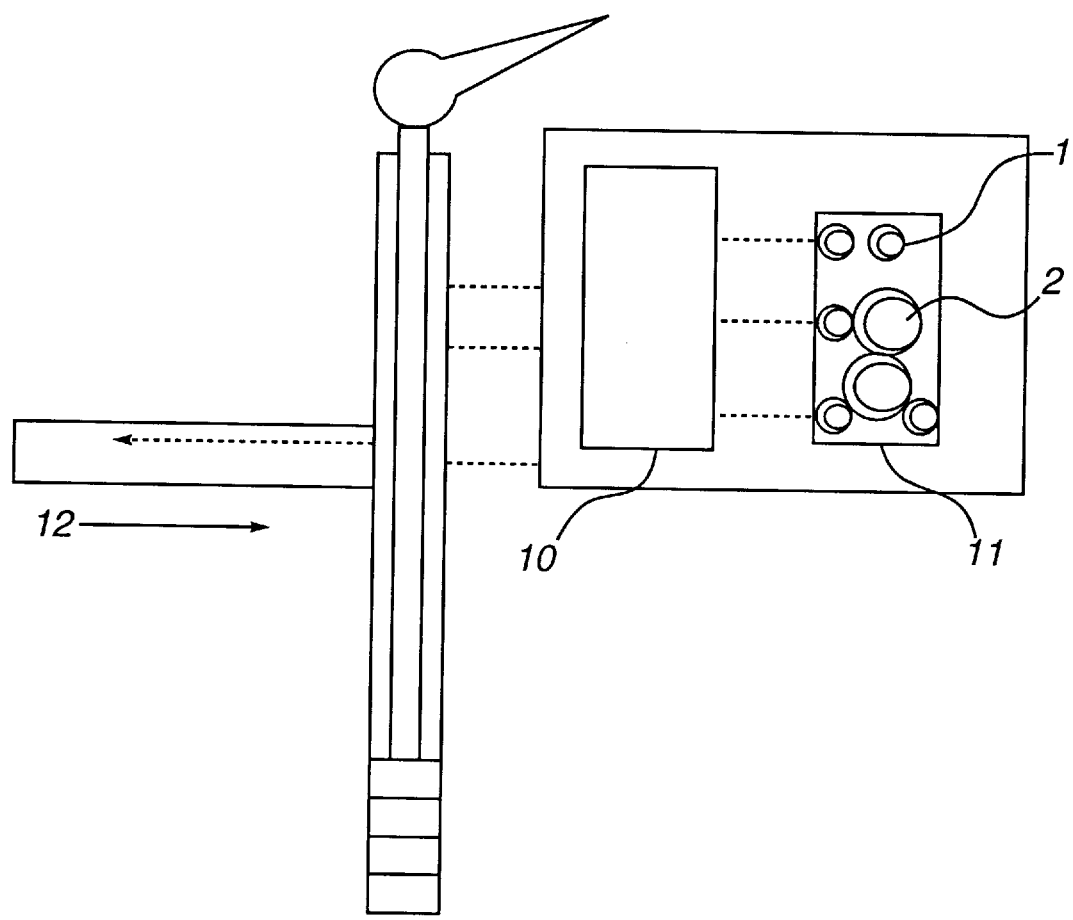
FIG. 4 is a representation drawing displaying how the instant manufacture may be used to prevent the build-up of paraffin wax in and upon the well head of producing oil wells; wherein the microshells 1 containing the organism 2 are contained in and comprise a specially designed fitting 10 or sieve 11 permitting retro-fit to existing well head structures 12.

In FIG. 3 is represented a further aspect of the combined apparatus. In this embodiment the microshell 1 containing the organism 2 may be a component in a second novel embodiment comprising a porous, buoyant container 5, e.g., a sack, constructed of natural or man-made fibers, resins, plastics, isomers, monomers, polymers, mylar, etc. or any versions of a suitable container (oblongated, square, etc.) which may afford convenient transportation and placement of the product in the area requiring remediation, both on land and in fluids, e.g. oceans and seas.

FIG. 3 shows the embodiment of FIG. 3 having contained therein a flotation mechanism 6, together therewith at various points along the instant manufacture are located fastening mechanisms, e.g., Velcro fasteners, or slots (male and female eye/hook configuration) or other such fastening mechanisms (snap button fasteners) which enable placement of a number of buoyant mechanisms of the present invention in a straight line, in a circle or a solid sheet, or in any shape which would be to the advantage of the user in terms of confining and remediating a dangerous fluid spill. For example, in the case of a spill at sea, a quantity of buoyant mechanisms of the present invention could be linked together surrounding and thereby containing the spill, thereby permitting the microshells containing the organism to function to dissolve the spill, thereby preventing devastation to the biosphere and ecosystems of the sea.

Likewise on land, an accidental spill could be encircled (preventing migration) and subsequently the entire spill area could be covered with buoyant mechanisms of the present invention configured into the shape of a tarpaulin, mitigating the severity of the incident to a minimum.

Although I claim a compartment comprising a floatation device, another aspect of the floatation device actually comprises additional microshells 1 which may be filled with buoyant gasses enabling floatation, thereby eliminating the need for separate buoyancy compartments. However, these compartments are desirable for obvious reasons.

The present invention is the subject of Disclosure Document Number JR-019 (my Serial Number) filed at the United States Patent and Trademark Office on Jul. 21, 1989 and the entire contents of the Disclosure Document, specifying the actual conception and discovery date, are incorporated herein by reference.

I claim:

1. A bioremediation system for the remediation of a petroleum hydrocarbon on water, said bioremediation system comprising: a buoyant container, said buoyant container including therein a plurality of bioremediation devices, each of said bioremediation devices comprising an organism capable of producing a substance for degrading a petroleum hydrocarbon and a shell containing said organism, said shell consisting essentially of a wax.

2. A system in accordance with claim 1 wherein said substance for degrading a chemical is an enzyme.

3. A system in accordance with claim 2 wherein said enzyme is lipase.

4. The system in accordance with claim 1 further comprising a nutrient contained in said shell.

5. The system of claim 1, wherein said organism is of the genus Candida, and of the specie *lypolytica.*

6. The system of claim 1, wherein said organism is of the genus Candida, and of the specie *guillermondii.*

7. The system of claim 1, wherein said organism is of the genus Candida, and of the specie *yarrowia.*

8. The system of claim 1, wherein said organism is of the genus Candida, and of the specie *albicans.*

9. The system of claim 1, wherein said shell is consists essentially of beeswax.

10. The system of claim 1 wherein said container further comprises fastening means adapted to enable fastening of said container to a second container.

11. The system of claim 10 wherein said container comprises means for enhancing floatation.

12. The system of claim 1, wherein said shell is a microsphere having a diameter between 0.20 and 1000 micrometers.

13. A method for degrading a petroleum hydrocarbon comprising: placing a plurality bioremediation devices in contact with said petroleum hydrocarbon, each of said bioremediation devices comprising an organism capable of degrading said petroleum hydrocarbon and a shell containing said organism, said shell consisting essentially of a wax.

* * * * *